United States Patent [19]

Child et al.

[11] Patent Number: 5,347,064
[45] Date of Patent: Sep. 13, 1994

[54] MULTIPLE SPLIT FEED ISOPARAFFIN-OLEFIN ALKYLATION

[75] Inventors: Jonathan E. Child, Sewell; Kenneth J. Del Rossi, Woodbury, both of N.J.; Albin Huss, Jr., Chadds Ford, Pa.; Robert S. Kurtas, Rancho Palos Verdes, Calif.

[73] Assignee: Mobil Oil Corporation, Fairfax, Va.

[21] Appl. No.: 45,435

[22] Filed: Apr. 12, 1993

[51] Int. Cl.⁵ .................................................. C07C 2/62
[52] U.S. Cl. ...................................... 585/716; 585/714; 585/717; 585/726
[58] Field of Search ................ 585/714, 716, 717, 726

[56] References Cited

U.S. PATENT DOCUMENTS

| | | |
|---|---|---|
| 1,593,716 | 7/1926 | Fox . |
| 2,296,370 | 9/1942 | Slotterbeck .............................. 196/10 |
| 2,296,371 | 9/1942 | Slotterbeck et al. ................... 196/10 |
| 2,345,095 | 3/1944 | Bruner et al. ...................... 260/683.4 |
| 2,804,491 | 8/1957 | May et al. .......................... 260/683.4 |
| 2,939,890 | 6/1960 | Hervert et al. ....................... 260/671 |
| 3,131,230 | 4/1964 | Herbert et al. ....................... 260/671 |
| 3,236,671 | 2/1966 | Dybalski et al. ..................... 106/277 |
| 3,251,902 | 5/1966 | Garwood et al. .............. 260/683.64 |
| 3,450,644 | 6/1969 | Lanewala et al. ................... 252/416 |
| 3,467,728 | 9/1969 | Hervert .............................. 260/683.2 |
| 3,549,557 | 12/1970 | Bolton et al. ........................ 252/455 |
| 3,644,565 | 2/1972 | Biale ................................. 260/683.43 |
| 3,647,916 | 3/1972 | Caesar et al. ..................... 260/683.43 |
| 3,655,813 | 4/1972 | Kirsch et al. ..................... 260/683.43 |
| 3,706,814 | 12/1972 | Kirsch et al. ..................... 260/683.43 |
| 3,738,977 | 6/1973 | Biale .................................... 260/94.9 |
| 3,800,003 | 3/1974 | Sobel ............................... 260/683.49 |
| 3,862,258 | 1/1975 | Huang et al. .................... 260/683.44 |
| 3,873,634 | 3/1975 | Hoffman .......................... 260/683.44 |
| 3,893,942 | 7/1975 | Yang ........................................ 252/411 |
| 3,917,738 | 11/1975 | Fenske et al. .................... 260/683.43 |
| 3,925,500 | 12/1975 | Wentzheimer .................. 260/683.44 |
| 3,977,621 | 8/1976 | Huffman ............................... 242/75.5 |
| 4,308,414 | 12/1981 | Hadgavkar et al. ................ 585/525 |
| 4,365,105 | 12/1982 | Morganson et al. .............. 585/525 |
| 4,394,296 | 7/1983 | Madgavkar et al. .............. 252/433 |
| 4,429,177 | 1/1984 | Morganson et al. .............. 585/525 |
| 5,245,101 | 9/1993 | Del Rossi et al. .................. 585/726 |

OTHER PUBLICATIONS

L. F. Albright et al., "Alkylation of Isobutane with C4 Olefins", 27 *Ind. Eng. Chem. Res.*, 381–397 (1988).
1 *Handbook of Petroleum Refining Processes* 23–28 (R. A. Meyers ed., 1986).

*Primary Examiner*—Asok Pal
*Attorney, Agent, or Firm*—Alexander J. McKillop; Dennis P. Santini; Robert B. Furr, Jr.

[57] ABSTRACT

An isoparaffin-olefin alkylation process is disclosed which improves alkylate quality by segregating the olefin feed into intermediate feedstreams which are enriched in propene, 1-butene, and/or 2-butenes with respect to the olefin feed, and alkylating these intermediate feedstreams in separate reaction zones at reaction temperatures specific to the olefin feed to increase the ratio of trimethylpentanes to dimethylhexanes in the resulting alkylate product.

19 Claims, 3 Drawing Sheets

MULTIPLE SPLIT FEED ISOPARAFFIN-OLEFIN ALKYLATION

FIELD OF THE INVENTION

This invention relates to a method for catalytically alkylating an isoparaffin with an olefin. More particularly, this application relates to a split-feed alkylation process for producing high octane gasoline.

BACKGROUND OF THE INVENTION

Isoparaffin-olefin alkylation upgrades two relatively low value feedstreams to form an isoparaffinic gasoline. This isoparaffinic alkylate is particularly useful as a component in so-called "clean" gasolines because it contains no aromatics, sulfur, or olefins, and is compatible with octane-enhancing oxygenates such as methyl tertiary butyl ether (MTBE) and tertiary amyl methyl ether (TAME).

Concentrated sulfuric or hydrofluoric acids have, in the past, been the catalysts of choice for isoparaffin-olefin alkylation. Sulfuric acid alkylation produces large volumes of spent acid waste, and the disposal costs for this spent material continue to rise. Hydrofluoric acid, on the other hand, is more readily regenerable, but, in the event of an accidental release, tends to vaporize and form clouds which can migrate for some distance. Years of industry experience have proven that HF can be handled safely, provided that the proper precautions are taken. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

With the increasing demands for octane and the increasing environmental concerns, it has been desirable to develop an alkylation process employing safer, more environmentally acceptable catalyst systems. Specifically, it is desirable to provide an industrially viable alternative to the currently used hydrofluoric and sulfuric acid alkylation processes. Consequently, substantial efforts have been made to develop a viable isoparaffin-olefin alkylation process which avoids the environmental and safety problems associated with sulfuric and hydrofluoric acid alkylation while retaining the alkylate quality and reliability characteristic of these well-known processes. Research efforts have been directed toward solid as well as liquid alkylation catalyst systems, as reflected in the following references.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as water-forming compound.

U.S. Pat. No. 3,450,644 discloses a method for regenerating a zeolite catalyst used in hydrocarbon conversion processes involving carbonium ion intermediates.

U.S. Pat. No. 3,549,557 describes alkylation of isobutane with $C_2$–$C_3$ olefins using certain crystalline aluminosilicate zeolite catalysts in a fixed-, moving- or fluidized bed system.

U.S. Pat. No. 3,644,565 discloses alkylation of a paraffin with an olefin in the presence of a catalyst comprising a Group VIII noble metal present on a crystalline aluminosilicate zeolite. The catalyst is pretreated with hydrogen to promote selectivity.

U.S. Pat. No. 3,647,916 describes an isoparaffin-olefin alkylation process featuring use of an ion-exchanged crystalline aluminosilicate, isoparaffin/olefin molar ratios below 3:1 and regeneration of the catalyst.

U.S. Pat. No. 3,655,813 discloses a process for alkylating $C_4$–$C_5$ isoparaffins with $C_3$–$C_9$ olefins using a crystalline aluminosilicate zeolite catalyst wherein a halide adjuvant is used in the alkylation reactor. The isoparaffin and olefin are introduced into the alkylation reactor at specified concentrations and catalyst is continuously regenerated outside the alkylation reactor.

U.S. Pat. No. 3,706,814 discloses another zeolite-catalyzed isoparaffin-olefin alkylation process and further provides for the addition of $C_5+$ paraffins such as Udex raffinate or $C_5+$ olefins to the alkylation reactor feed and the use of specific reactant proportions, halide adjuvants, etc.

U.S. Pat. No. 3,236,671 discloses an alkylation reaction wherein crystalline aluminosilicate zeolites having silica to alumina mole ratios above 3 are used. The reference also discloses the use of various metals exchanged and/or impregnated on such zeolites.

U.S. Pat. No. 3,738,977 discloses alkylation of paraffins with ethylene using a zeolite catalyst which possesses a Group VII metal component. The catalyst is pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone. Thereafter, the reactants are passed concurrently with the catalyst so that a controlled amount of olefin is adsorbed into the catalyst before the combination of reactants and catalyst is introduced into an alkylation zone. This controlled olefin adsorption is thought to prevent polymerization of the olefin during alkylation.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large-pore zeolite with a Lewis acid is reported to increase the activity and selectivity of the zeolite, thereby effecting alkylation with high olefin space velocity and low isoparaffin/olefin ratio. According to the patent, problems arise in the use of solid catalyst in that they appear to age rapidly and cannot perform effectively at high olefin space velocity and the patent teaches the above solution to rectify the problem utilizing a zeolite alkylation catalyst.

The article entitled "Fixed Bed Catalytic Process to Produce Synthetic Lubricants from Decene-1", IND. ENG. CHEM. PROD. RES. DEV., Vol. 22, No. 4 (1983) teaches oligomerizing olefin to produce fluids with lubricating properties using a silica-$BF_3$-water catalyst. The authors further teach that with this system much of the $BF_3$ can be recycled to minimize $BF_3$ consumption and disposal problems. The reference teaches that water is a necessary component of the system and that in its absence a $BF_3$-silica catalyst rapidly deactivates.

In U.S. Pat. No. 4,308,414, an olefin, such as 1-decene, is oligomerized in the presence of a three-component catalyst comprising boron trifluoride, a minute amount of water and a particulate absorbent material such as silica to a lubricating product predominating in those oligomer fractions having viscosities within the lubricating oil range such as the trimer and tetramet.

U.S. Pat. No. 4,429,177 further relates to a method for making lubricating oil utilizing a catalyst comprising boron trifluoride, a minute amount of elemental oxygen and a particulate absorbent material such as silica.

U.S. Pat. No. 3,977,621 relates to oligomerization of olefins catalyzed by boron trifluoride which is controlled to yield desired trimer as a dominant lubricant product by adding small amounts of ester together with water or alcohol promoter.

U.S. Pat. No. 4,365,105 also relates to oligomerizing an olefin in the presence of three-component catalyst used in making lubricating oils which comprises a particular silica absorbent with boron trifluoride and water absorbed on the silica.

U.S. Pat. No. 4,394,296 relates to a three-component catalyst used in making lubricating oils which comprises a particular silica absorbent with boron trifluoride and water absorbed on the silica.

U.S. Pat. No. 2,939,890 discloses a process for alkylating an aromatic hydrocarbon with an olefin-acting compound at alkylation conditions in the presence of an alkylation catalyst comprising boron trifluoride-modified alumina. Subsequently, U.S. Pat. No. 3,131,230 discloses the importance of the presence of small amounts of water for maintaining catalyst activity. Both of these patents are limited to aromatic alkylation processes.

U.S. Pat. No. 2,804,491 relates to isoparaffin-olefin alkylation to make gasoline at temperatures between $-20°$ and $150°$ F. utilizing a two-component catalyst comprising essentially excess $BF_3$ with a "silica stabilized gel alumina." No activators are taught.

U.S. Pat. Nos. 3,251,902 and 3,893,942, as well as French Patent 1,593,716 and the article by Kirsh and Potts, DIV. OF PET. CHEM. A.C.S. 15, A109 (1970) address alkylation in the presence of zeolite-based catalyst systems.

U.S. Pat. No. 3,467,728 relates to a process for isomerizing olefinic hydrocarbon, such as 1-butene or 1-pentene by contacting the hydrocarbon with a catalyst comprising a crystalline alumina silicate combined with a substantially anhydrous boron halide.

U.S. Pat. No. 3,800,003 relates to a process for producing an alkylation reaction product from an isoparaffinic reactant and an olefinic reactant containing 1-butene, 2-butene and isobutene which includes passing the olefinic reactant through an isomerization zone. The isomerization catalyst comprises a crystalline aluminosilicate combined with a substantially anhydrous boron halide which can be boron trifluoride. Conventional catalysts are utilized for the alkylation reaction and include sulfuric acid and hydrogen fluoride catalyst which have the disadvantages set forth above.

Catalyst complexes comprising $BF_3$ as well as $BF_3:H_3PO_4$ adducts have been proposed, and are discussed in greater detail below. While these catalysts effectively overcome many of the safety and environmental drawbacks of sulfuric and hydrofluoric acid alkylation systems, the volume and quality of $BF_3$ alkylates have not, in the past, proven comparable to that of sulfuric or hydrofluoric acid alkylates. Further, the $BF_3$-catalyzed isobutane-butene alkylation processes typically require high isoparaffin:olefin feed ratios of at least about 5:1 to produce an alkylate gasoline product of acceptable quality.

U.K. Patent 545,441, assigned to Standard Oil Development Company, teaches a $BF_3:H_3PO_4$ catalyzed isoparaffin-olefin alkylation process.

U.S. Pat. No. 2,345,095 to Bruner teaches a paraffin-olefin alkylation process catalyzed by a boron trifluoride-water complex, represented by the formula $BF_3:nH_2O$, where n is preferably from 1 to 1.5.

U.S. Pat. Nos. 2,296,370 and 2,296,371 to Slotterbeck disclose a $BF_3:H_2O:HF$ catalyst system and an isoparaffin-olefin alkylation process employing the same. The catalyst system is said to avoid yield loss due to oxidation of the resulting alkylate product.

U.K. Patent 550,711 teaches a process for increasing the activity of at least partially spent $BF_3:H_2O$ catalyst systems for reuse in an organic condensation reaction. Briefly, the process volatilizes $BF_3$ from the liquid catalyst mass to the extent required to promote separation of a distinct hydrocarbon phase from the catalyst mass. This hydrocarbon phase is then decanted off and fresh $BF_3$ is added to restore catalytic activity.

Canadian Patent 424,000 teaches a process for producing gasoline boiling range hydrocarbons from isobutane and a normally gaseous olefin by absorbing the olefin in phosphoric acid of at least 75 weight percent concentration with an amount of isobutane equal to at least three moles of isobutane per mole of alkyl phosphate in the presence of a catalytic mixture of phosphoric acid and boron halide at temperature between $20°$ C. and $60°$ C.

U.S. Pat. No. 3,873,634 to Hoffman teaches a method of increasing the rate of ethylene alkylation by isobutane by carrying out the reaction simultaneously with the alkylation of a small amount of a higher weight olefin with isobutane in the presence of a $BF_3:H_3PO_4$ catalyst complex at low temperature and pressure.

U.S. Pat. No. 3,925,500 to Wentzheimer discloses a combined acid alkylation and thermal cracking process employing a $BF_3:H_3PO_4$ acid catalyst in which unconverted propane and ethane from the alkylation process are converted, for example, to propylene and ethylene which are subsequently alkylated with isobutane to evolve a valuable liquid fuel.

SUMMARY OF THE INVENTION

The present invention provides a process for alkylating an isoparaffin with an olefin in the presence of a catalyst comprising $BF_3$ and $H_3PO_4$. The process feed contains propene, 1-butene, and 2-butene, and may optionally further contain isobutene.

The invention comprises, in a first aspect, a process for alkylating an isoparaffin with an olefin comprising the steps of:

(a) providing a feed comprising propene, 1-butene, and 2-butenes;

(b) separating a first intermediate stream enriched in propene from said feed;

(c) separating a second intermediate stream enriched in 1-butene from said feed;

(d) separating a third intermediate stream enriched in 2-butenes from said feed;

(e) contacting said first intermediate stream with excess isobutane in a first reaction zone containing $BF_3$ and $H_3PO_4$ in $BF_3:H_3PO_4$ molar ratios of from about 0.5:1 to about 1.5:1 under isobutane-propene alkylation conversion conditions including temperature $T_1$ to produce a first alkylate product enriched in isoparaffins having more than 4 carbon atoms;

(f) contacting said second intermediate stream with excess isobutane in a second reaction zone containing $BF_3$ and $H_3PO_4$ in $BF_3:H_3PO_4$ molar ratios of from about 0.5:1 to about 1.5:1 under isobutane-1-butene alkylation conversion conditions including temperature $T_2$, wherein $T_2<T_1$, to produce a second alkylate product enriched in isoparaffins having more than 5 carbon atoms;

(g) contacting said third intermediate stream with excess isobutane in a third reaction zone containing $BF_3$ and $H_3PO_4$ in $BF_3:H_3PO_4$ molar ratios of from about 0.5:1 to about 1.5:1 under isobutane-2-butenes alkylation conversion conditions including temperature $T_3$, wherein $T_3<T_2<T_1$, to produce a third alkylate product enriched in isoparaffins having more than 5 carbon atoms; and (h) recovering said alkylate products from steps (e), (f), and (g).

The total gasoline product produced by the process of the invention may be still further upgraded by selectively converting feed isobutene to methyl tertiary butyl ether upstream of the alkylation process steps. The invention comprises, in a second aspect, a process for upgrading a mixed olefin stream to a high octane motor gasoline blending stock comprising the steps of:

(a) providing a feed comprising propene, 1-butene, 2-butenes, and isobutene;

(b) separating a first intermediate stream enriched in propene from said feed to evolve a second propene-lean intermediate stream;

(c) contacting said second propene-lean intermediate stream with methanol in a first reaction zone containing an etherification catalyst under conversion conditions to selectively convert isobutene to methyl tertiary butyl ether;

(d) recovering methyl tertiary butyl ether from said propene-lean intermediate stream;

(e) separating a third intermediate stream enriched in 1-butene from said feed;

(f) separating a fourth intermediate stream enriched in 2-butenes from said feed;

(g) contacting said first intermediate stream with excess isobutane in a first reaction zone containing $BF_3$ and $H_3PO_4$ in $BF_3:H_3PO_4$ molar ratios of from about 0.5:1 to about 1.5:1 under isobutane-propene alkylation conversion conditions including temperature $T_1$ to produce a first alkylate product enriched in isoparaffins having more than 4 carbon atoms;

(h) contacting said third intermediate stream with excess isobutane in a second reaction zone containing $BF_3$ and $H_3PO_4$ in $BF_3:H_3PO_4$ molar ratios of from about 0.5:1 to about 1.5:1 under isobutane-1-butene alkylation conversion conditions including temperature $T_2$, wherein $T_2<T_1$, to produce a second alkylate product enriched in isoparaffins having more than 5 carbon atoms;

(i) contacting said fourth intermediate stream with excess isobutane in a third reaction zone containing $BF_3$ and $H_3PO_4$ in $BF_3:H_3PO_4$ molar ratios of from about 0.5:1 to about 1.5:1 under isobutane-2-butenes alkylation conversion conditions including temperature $T_3$, wherein $T_3<T_2<T_1$, to produce a third alkylate product enriched in isoparaffins having more than 5 carbon atoms; and (j) recovering said alkylate products from steps (g), (h), and (i).

The invention provides, in a third aspect, a process for alkylating an isoparaffin with an olefin comprising the steps of:

(a) providing a feed comprising propene, 1-butene, and 2-butenes;

(b) separating a first intermediate stream enriched in propene and 1-butene from said feed;

(c) separating a second intermediate stream enriched in 2-butenes from said feed;

(d) contacting said first intermediate stream with excess isobutane in a first reaction zone containing $BF_3$ and $H_3PO_4$ in $BF_3:H_3PO_4$ molar ratios of from about 0.5:1 to about 1.5:1 under a first set of alkylation conversion conditions including temperature $T_1$ to produce a first alkylate product enriched in isoparaffins having more than 4 carbon atoms;

(e) contacting said second intermediate stream with excess isobutane in a second reaction zone containing $BF$ and $H_3PO_4$ in $BF_3:H_3PO_4$ molar ratios of from about 0.5:1 to about 1.5:1 under a second set of alkylation conversion conditions including temperature $T_2$, wherein $T_2<T_1$, to produce a second alkylate product enriched in isoparaffins having more than 5 carbon atoms; and (g) recovering said alkylate products from steps (d) and (e).

DETAILED DESCRIPTION

Figure 1:
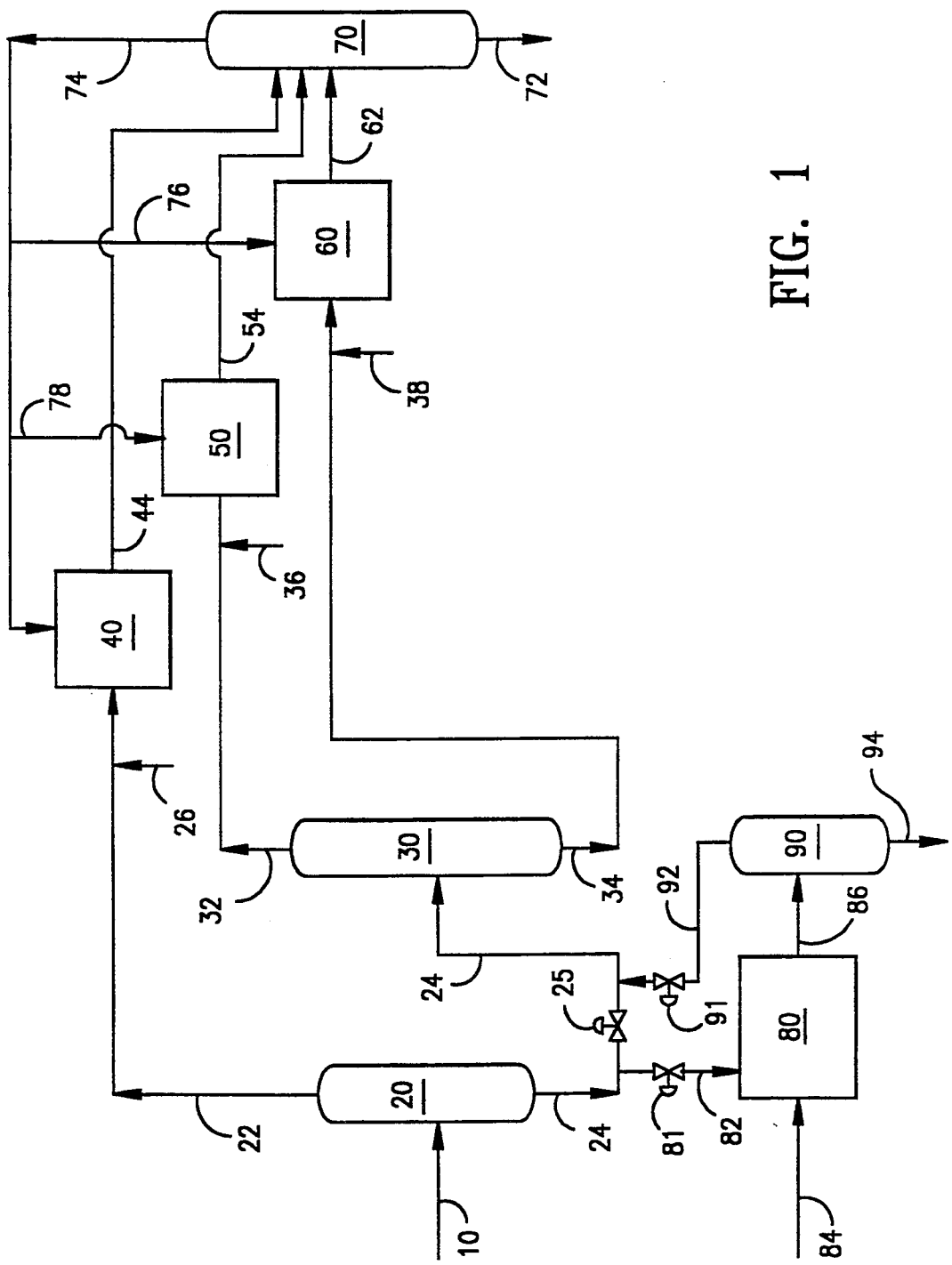
FIG. 1 is a simplified schematic diagram showing major processing steps of one embodiment of the present invention.

The process of the invention alkylates an isoparaffin with an olefin in the presence of a catalyst comprising $BF_3$ and $H_3PO_4$. The olefinic feed contains propene, 1-butene, and 2-butene. If the olefin feed contains significant quantities of isobutene, and if methanol is readily available, the isobutene may be selectively upgraded to methyl tertiary butyl ether upstream of the alkylation reaction zones.

Feedstocks useful in the present alkylation process generally include at least one isoparaffin and at least three olefins. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least three olefins having from 2 to 12 carbon atoms. Representative examples of such olefins include butene-2, isobutylene, butene-1, propylene, ethylene, hexene, octene, and heptene, merely to name a few. The preferred olefins include the $C_3$ and $C_4$ olefins, for example, propene, 1-butene, 2-butene, and isobutene with mixtures of all four of these olefins being the most preferred. Suitable feedstocks for the process of the present invention are described in U.S. Pat. No. 3,862,258 to Huang et al. at column 3, lines 44–56, the disclosure of which is incorporated by reference as if set forth at length herein.

The weight ratio of isoparaffin to olefin in the total feed to the alkylation reaction zone is generally between 1.5:1 and 100:1, preferably between about 5:1 and about 50:1. Suitable total fresh feedstocks contain isoparaffin and olefin in isoparaffin:olefin weight ratio of from greater than about 1:1 up to about 10:1.

The total feed to the alkylation reaction zone contains both the total fresh isoparaffin:olefin feed and the recycled hydrocarbons from the alkylation reactor including unreacted isoparaffin as well as alkylated product.

The term "recycle ratio" as used herein is defined as follows:

Recycle Ratio = (Weight per unit time Total Hydrocarbon Recycled From the Reactor)/(Weight per unit time of Fresh Feed).

Recycle ratios useful in the present invention typically fall within the range of from about 0.5 to about 100, preferably from about 2 to about 10.

Process Conditions

A first embodiment of the invention separates the olefinic feed into three streams. The first enriched in propene, the second enriched in 1-butene, and the third enriched in 2-butenes. In this first embodiment, each stream is charged to a separate reaction zone, and each reaction zone is operated at a different temperature, with propene-isobutane alkylation at the highest temperature, 1-butene-isobutane alkylation at a lower temperature, and 2-butenes-isobutane alkylation at the lowest of the three reaction temperatures.

A second embodiment of the invention includes an etherification step upstream from the alkylation reactions to selectively remove isobutene from the olefinic feed. Process conditions for the alkylation reaction zones are essentially the same as for the first embodiment.

A third embodiment of the invention splits the olefinic feed into a first stream enriched in propene and 1-butene and a second stream enriched in 2-butenes. In this second embodiment, the two olefinic streams are charged to separate alkylation reaction zones. The propene/1-butene/isobutane reaction zone is maintained at higher temperature than the 2-butenes/isobutane alkylation reaction zone.

| Propene-Isobutane Alkylation | | |
|---|---|---|
| | Broad | Preferred |
| Temperature, °F. | 10 to 150 | 80 to 120 |
| Pressure, psia | 50 to 1500 | 100 to 500 |
| WHSV, hr$^{-1}$ Isobutane:propene | .01 to 10 | 0.1 to 5 |
| Molar feed ratio, Isoparaffin:olefin | 1.5:1 to 100:1 | 5:1 to 20:1 |

| 1-Butene-Isobutane Alkylation | | |
|---|---|---|
| | Broad | Preferred |
| Temperature, °F. | 10 to 140 | 80 to 110 |
| Pressure, psia | 50 to 1500 | 100 to 500 |
| WHSV, hr$^{-1}$ Isobutane:1-butene | 0.01 to 10 | 0.1 to 5 |
| Molar feed ratio, Isoparaffin:olefin | 1.5:1 to 100:1 | 5:1 to 20:1 |

| 2-Butene-Isobutane Alkylation | | |
|---|---|---|
| | Broad | Preferred |
| Temperature, °F. | −20 to 80 | 20 to 60 |
| Pressure, psia | 50 to 1500 | 100 to 500 |
| WHSV, hr$^{-1}$ Isobutane:2-butene | 0.01 to 10 | 0.1 to 5 |
| Molar feed ratio, Isoparaffin:olefin | 1.5:1 to 100:1 | 5:1 to 20:1 |

Operating pressure is generally controlled to maintain the reactants in the liquid phase, and typically falls in the range of from about 50 to about 1500 psig, preferably from about 100 to about 500 psig.

Hydrocarbon and catalyst flow through the alkylation zones is typically controlled to provide weight hourly space velocity (WHSV) sufficient to convert about 99 percent by weight of fresh olefin to alkylate product. Typical WHSV values typically fall within the range of from about 0.01 to about 10 hr$^{-1}$.

The particular operating conditions used in the present process will depend on the specific alkylation reaction being effected. Process conditions such as temperature, pressure, space velocity and molar ratio of the reactants will effect the characteristics of the resulting alkylate, and may be adjusted within the disclosed ranges by those skilled in the art with only minimal trial and error.

Etherification

In the preferred embodiments of this invention methanol is reacted with the hydrocarbon feed containing olefins and particularly isoolefins such as isobutene to produce methyl tertiary butyl ethers.

Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites such as zeolite Beta and ZSM-5. Typical hydrocarbon feedstock materials for etherification reactions include olefinic streams, such as FCC light naphtha and butenes rich in iso-olefins. These aliphatic streams are produced in petroleum refineries by catalytic cracking of gas oil or the like.

In the process of this invention the term light alkanol includes methanol, ethanol, propanols and butanols, such as isopropanol and 1-butanol.

Processes for producing and recovering MTBE and other methyl tertiary alkyl ethers from $C_4$–$C_7$ isoolefins are known to those skilled in the art, such as disclosed in U.S. Pat. No. 4,544,776 (Osterburg, et al.) and 4,603,225 (Colaianne et al.). Various suitable extraction and distillation techniques are known for recovering ether and hydrocarbon streams from etherification effluent.

In the process for catalytic conversion of oxygenate and/or olefins to heavier hydrocarbons by catalytic oligomerization using an acidic metallosilicate solid, including acid crystalline zeolite having the structure of ZSM-5, process conditions can be varied to favor the formation of either gasoline, distillate, lube range products, aromatics or the interconversion of light olefins.

Embodiments

Referring now to FIG. 1, a mixed olefin feed 10 containing propene, 1-butene, 2-butenes, and isobutene flows to propene/butenes fractionator 20 where it separates into an overhead stream enriched in propene, which is withdrawn through line 22, and a bottom stream enriched in butenes, which is withdrawn through line 24.

Isobutene may optionally be removed from the propene/butenes fractionator bottom stream 24 by opening valves 81 and 91 and at least partially closing valve 25 to flow all or a portion of the bottom stream from line 24 through line 82 to catalytic etherification reactor 80. Methanol enters etherification reactor 80 through line 84 and selectively reacts with the isobutylene in the feed to produce a partially etherified product stream which flows through line 86 to fractionator 90 where a bottom stream 94 enriched in methyl tertiary butyl ether is separated from an overhead stream 92 which is enriched in n-butenes.

The effluent from line 24 enters fractionator 30 where it is separated into an overhead stream 32 enriched in 1-butene (b.p. −6.3° C.) and a bottom stream 34 enriched in 2-butenes (trans-2-butene, b.p. 1° C.; cis-2-butene, b.p. 3.7° C.). Fractionator 30 may optionally be replaced by a selective sorbent process for separating 1-butene from 2-butene.

The overhead stream from propene/butenes fractionator 20, which is enriched in propene, is mixed with fresh isobutane from line 26, and flows to a first alkylation reaction stage 40 together with recycled isobutane from line 74. Reaction temperature within the first alkylation reactor is controlled at about 100° F. Unreacted isobutane together with alkylate product enriched in $C_7$ isoparaffins is withdrawn through line 44 and flows to deisobutanizer 70 which separates the alkylation reaction stage effluents into an overhead recycle stream enriched in isobutane and a bottom stream enriched in $C_5+$ alkylate gasoline. The isobutane-enriched overhead stream is recycled through line 74 while the $C_5+$ alkylate gasoline stream is routed to gasoline blending and storage facilities (not shown).

The 1-butene-enriched stream in line 32 and the isobutane-enriched recycle stream in line 78 (optionally supplemented with fresh isobutane from line 36 to maintain an overall isobutane:1-butene molar ratio of about 10:1) flow to the second alkylation reaction stage 50, where essentially all of the 1-butene is upgraded to alkylate. The reaction zone effluent stream, enriched containing unreacted isobutane and alkylate is withdrawn through line 54 and charged to deisobutanizer 70. If the isobutane/2-butene mixture in line 34 downstream from line 52 contains sufficient isobutane to maintain a feed isobutane:2-butene ratio of at least about 10:1, then the mixture is charged directly to the third alkylation reaction stage 60. If the isobutane:2-butene ratio falls below about 10:1, recycled isobutane may be added through line 76 or fresh isobutane may be added via line 38. Reactor effluent from the third alkylation reaction stage flows through line 62 to deisobutanizer 70, which recovers alkylate gasoline as the bottom stream through line 72 as described above.

EXAMPLES

The following experiments were carried out in a continuous stirred autoclave. In a typical experiment, 130 grams of orthophosphoric acid were loaded into a 300 cc autoclave. The autoclave was filled with isobutane, cooled to 50° F., and pressurized to 150 psig while stirring at 1000 rpm. The reactor contents were then saturated with BF overnight at 25 cc/min. The resulting $BF_3:H_3PO_4:H_2O$ catalyst contained 54 wt % $BF_3$. A pre-mixed 10/1 wt/wt isobutane/olefin feed was then introduced at a rate of 142 grams/hr (0.05 gms olefin/gm $BF_3:H_3PO_4:H_2O/hr$) and the $BF_3$ feed rate was reduced to 0.17 grams/hr (0.1 wt % of total feed). The liquid product was collected in a receiver chilled to 32° F. The receiver off-gas was passed through a column (36"×4" pyrex glass) filled with indicating grade soda lime ($Ca(OH)_2$) to remove $BF_3$, and finally through a wet test meter.

EXAMPLES 1-3

The results of Examples 1-3 showed that increasing reactor temperature reduced alkylate octane for an isobutane-2-butene feed. The data in Table 1 give the resulting alkylate properties for reactor temperatures of 32°, 50° and 90° F.

TABLE 1

| EFFECT OF TEMPERATURE WITH 2-BUTENE FEEDS | | | |
|---|---|---|---|
| Example No. | 1 | 2 | 3 |
| Reactor Temperature, °F. | 32 | 50 | 90 |
| Alkylate Composition, wt % | | | |
| $C_5-C_7$ | 5.6 | 6.9 | 13.9 |
| $C_8$'s | 88.9 | 87.5 | 74.9 |
| $C_9+$ | 5.5 | 5.6 | 11.2 |
| TMP/DMH | 6.9 | 6.0 | 2.7 |
| Olefin Conversion, wt % | 98.5 | 99.4 | 100.0 |
| $C_5+$ Octane (R + M/2) | 96.8 | 96.3 | 91.3 |

EXAMPLES 4 AND 5

Examples 4 and 5 compare 1-butene and 2-butene alkylates produced with $BF_3$ phosphoric acid (0.15 Acid/Oil vol/vol in reactor) using 10/1 wt/wt isobutane/butene feeds at 50° F. Results are shown in Table 2. With 5200 ppm $BF_3$ cofeed, the ratio of trimethylpentanes to dimethylhexanes (TMP/DMH) in the 1-butene alkylate product was 0.3, and the alkylate octane was 75.8 R+M/2. A 2-butene feed at identical conditions yielded alkylate with a TMP/DMH ratio of 4.1 and an octane of 94.4 R+M/2. Yield of $C_5+$ alkylate (grams $C_5+$ per gram $C_4=$converted) was on average 1.9 for alkylation of 1-butene with isobutane and 2.0 for alkylation of the 2-butene isomer. Consistent with the lower yield, 1-butene alkylates contained more heavy hydrocarbons ($C_9+$) and less cracked product ($C_5-C_7$) than 2-butene alkylates.

TABLE 2

| COMPARISON OF 1-AND 2-BUTENE ALKYLATES | | |
|---|---|---|
| Example No. | 4 | 5 |
| Olefin Feed | 1-$C_4=$ | 2-$C_4=$ |

TABLE 2-continued

| COMPARISON OF 1-AND 2-BUTENE ALKYLATES | | |
|---|---|---|
| Example No. | 4 | 5 |
| Alkylate Composition, wt % | | |
| $C_5$-$C_7$ | 2.1 | 9.3 |
| $C_8$'s | 86.9 | 86.2 |
| $C_9+$ | 11.0 | 5.5 |
| TMP/DMH | 0.3 | 4.1 |
| Olefin Conversion, wt % | 100 | 99.8 |
| $C_5+$ Octane (R + M/2) | 75.8 | 94.4 |

EXAMPLES 6 AND 7

Examples 6 and 7 show the effect of temperature on 1-butene alkylate quality. Table 3 presents data obtained with the $BF_3$:$H_3PO_4$:$H_2O$ catalyst (1/1 Acid/Oil vol/vol in reactor) using a 10/1 isobutane/1-butene feed with 1000 ppmw $BF_3$ cofeed at 50° and 80° F. The TMP/DMH ratio in the alkylate product increased from 0.5 to 0.9 upon raising temperature to 80° F., while the yield of heavy $C_9+$ product decreased. Octanes were 85.7 and 80.5 R+M/2 at 80° and 50° F., respectively.

TABLE 3

| EFFECT OF REACTION TEMPERATURE ON 1-BUTENE PRODUCT | | |
|---|---|---|
| Example No. | 6 | 7 |
| Temperature, °F. | 50 | 80 |
| Alkylate Composition, wt % | | |
| $C_5$-$C_7$ | 2.3 | 3.6 |
| $C_8$ | 84.6 | 83.9 |
| $C_9+$ | 13.1 | 9.9 |
| TMP/DMH | 0.5 | 0.9 |
| $C_5+$ Octane (R + M/2) | 80.5 | 85.7 |

Figure 2:
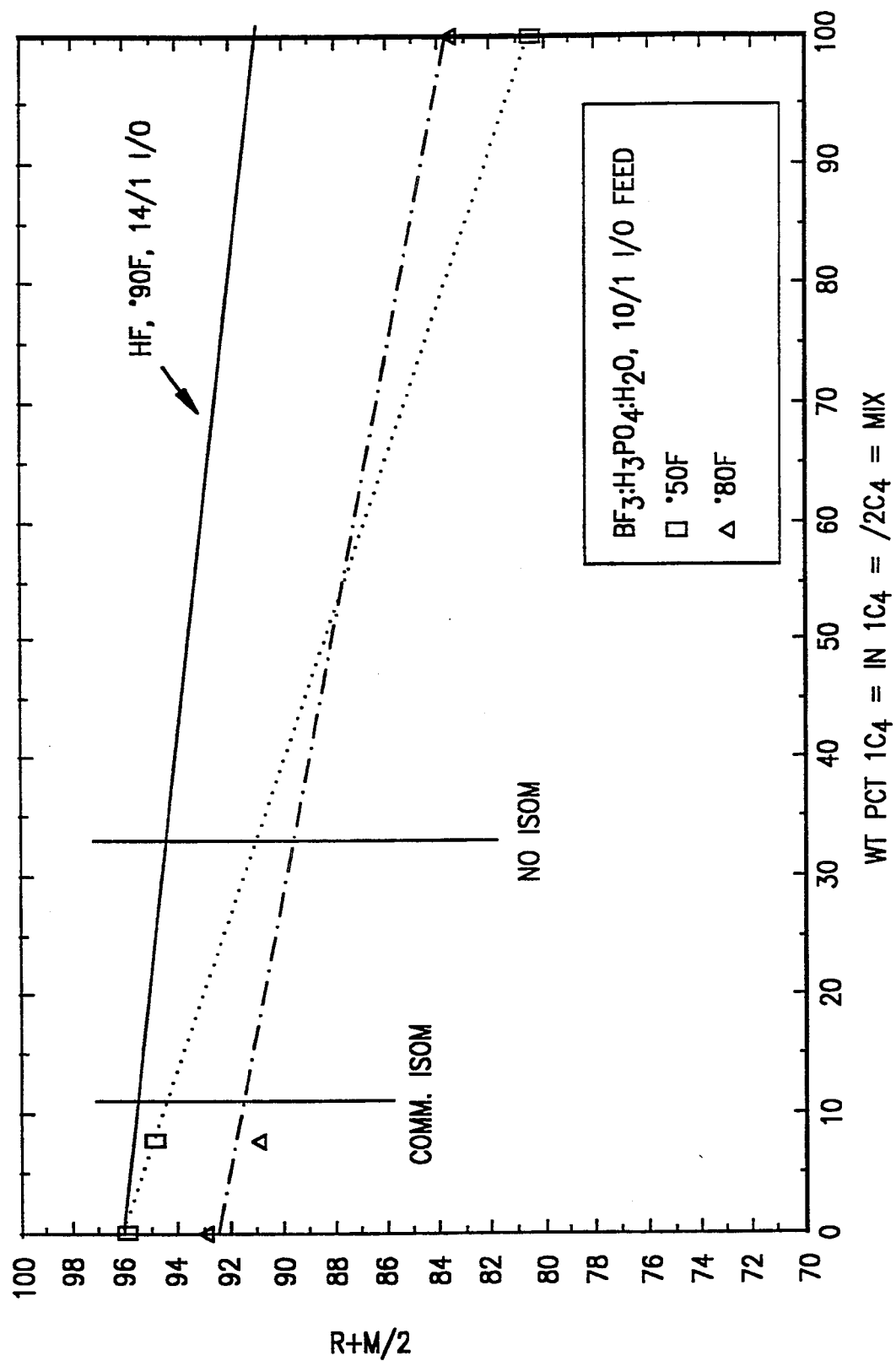
FIG. 2 shows alkylate octane as a function of 1-butene concentration in a 10/1 wt/wt isobutane/1-, 2-butene mixed feed in the presence of a $BF_3:H_3PO_4:H_2O$ catalyst at a 1/1 acid/oil ratio.

Alkylate octane for the $BF_3$:$H_3PO_4$:$H_2O$ catalyst (1/1 Acid/Oil in reactor) is plotted as a function of 1-butene concentration in a 10/1 wt/wt isobutane/1-, 2-butene mixed feed in FIG. 2. The vertical lines show the octane potential of the $BF_3$:$H_3PO_4$:$H_2O$ catalyst with and without isomerization of 1-butene in a typical commercial butene feed. Current commercial butene isomerization processes produce butene streams with a minimum of about 11 wt % 1-butene. Octanes for HF alkylates from 1- and 2-butene-containing feeds are plotted for comparison with the $BF_3$ phosphoric acid data. Operating at 80° F. with a 10/1 isobutane/mixed butene feed without butene isomerization yields about a 4 R+M/2 lower octane for the $BF_3$ phosphoric acid catalyst compared to HF at 90° F. with a 14/1 isobutane/butene feed.

EXAMPLES 8-11

Examples 8–11 show that temperature strongly effects alkylation performance with propylene-containing feeds. Table 4 lists data obtained at 50° and 80° F. with $BF_3$ phosphoric acid catalyst (1/1 Acid/Oil in reactor, 1000 ppmw $BF_3$ cofeed) using pure $C_3=$ and mixed $C_3=/2-C_4=$containing 10/1 isobutane/olefin feeds. In general, production of heavy $C_9+$ alkylate from propylene-containing feeds decreased as temperature was raised. With pure propylene-containing feed, alkylate octane increased as temperature was raised due to a marked reduction in the amount of low octane $C_9+$ product. A corresponding increase in $C_5+$ alkylate yield was also observed upon raising reaction temperature. Yield of $C_5+$ alkylate increased from 1.6 to 2.0 while $C_9+$ in the alkylate product decreased from 26 to 15 wt % upon raising reaction temperature from 50° to 80° F. In contrast to results with pure propylene-containing feed, alkylate octane with mixed $C_3=/2-C_4=$feed decreased as temperature was raised due to higher production of the lower octane $C_7$ isomer, 2,4-dimethyl-pentane (83.5 R+M/2) in preference to 2,3-dimethyl-pentane (89.8 R+M/2).

TABLE 4

| EFFECT OF REACTION TEMPERATURE ON $C_3=$ ALKYLATE | | | | |
|---|---|---|---|---|
| Example No. | 8 | 9 | 10 | 11 |
| Feed Olefin | $C_3=$ | $C_3=$ | $C_3=/2-C_4=$ | $C_3=/2-C_4=$ |
| Temperature, °F. | 50 | 80 | 50 | 80 |
| Alkylate Comp., wt % | | | | |
| $C_5/C_6$ | 4.2 | 5.5 | 4.3 | 5.9 |
| $C_7$ | 51.5 | 53.6 | 19.5 | 18.6 |
| $C_8$ | 18.1 | 25.9 | 65.9 | 65.5 |
| $C_9+$ | 26.3 | 15.0 | 10.4 | 10.1 |
| Hydrogen Transfer, % | 9.6 | 16.6 | 7.7 | 10.0 |
| TMP/DMH | 6.3 | 3.4 | 6.7 | 3.3 |
| Yield ($C_5+/C_3=$ Conv.) | 1.6 | 2.0 | 1.8 | 1.7 |
| $C_5+$ Octane (R + M/2) | 86.1 | 89.2 | 93.6 | 90.6 |

Figure 3:
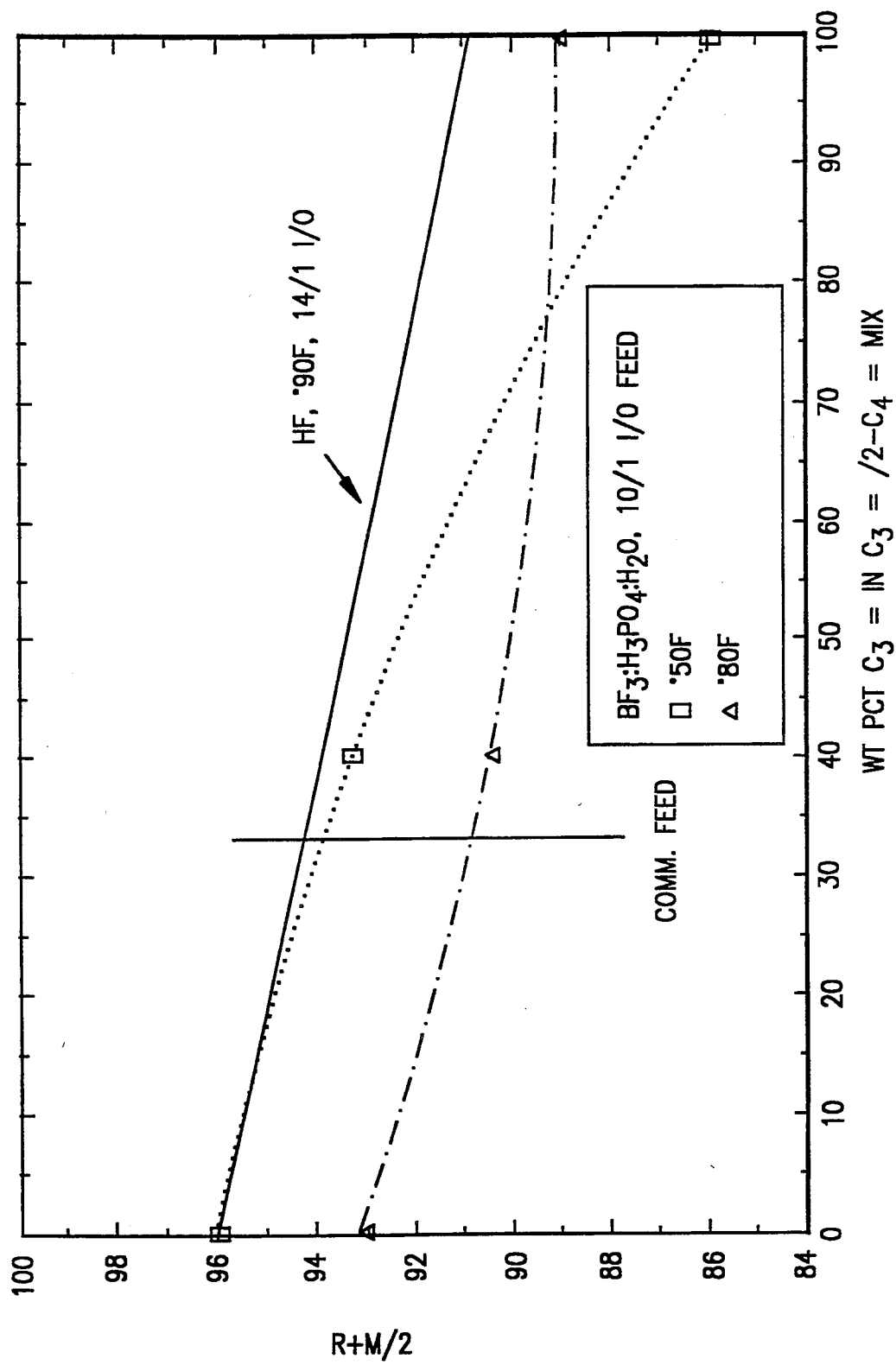
FIG. 3 shows alkylate octane as a function of propene concentration for a mixed feed containing isobutane, propene, and 2-butene in a 10/1 ratio of isobutane/total olefins.

Propylene alkylate octane is plotted as a function of $C_3=$concentration in a 10/1 wt/wt isobutane/mixed $C_3=/2-C_4=$feed in FIG. 3. Octanes for HF alkylates (90° F., 14/1 isobutane/olefin) from propylene- and 2-butene-containing feeds are plotted for comparison with the $BF_3$ phosphoric acid data.

Changes and modifications in the specifically described embodiments can be carried out without departing from the scope of the invention which is intended to be limited only by the scope of the appended claims.

What is claimed is:

1. An isoparaffin-olefin alkylation process comprising the steps of:
   (a) providing a feed comprising propene, 1-butene, and 2-butenes;
   (b) separating a first intermediate stream from said feed, said first intermediate stream being enriched in propene in comparison to said feed;
   (c) separating a second intermediate stream from said feed, said second intermediate stream being enriched in 1-butene in comparison to said feed;
   (d) separating a third intermediate stream from said feed, said third intermediate stream being enriched in 2-butenes in comparison to said feed;
   (e) contacting said first intermediate stream with excess isobutane in a first reaction zone containing $BF_3$ and $H_3PO_4$ in $BF_3$:$H_3PO_4$ molar ratios of from about 0.5:1 to about 1.5:1 under isobutane-propene alkylation conversion conditions including temperature $T_1$ to produce a first alkylate product enriched in isoparaffins having more than 4 carbon atoms;
   (f) contacting said second intermediate stream with excess isobutane in a second reaction zone containing $BF_3$ and $H_3PO_4$ in $BF_3$:$H_3PO_4$ molar ratios of from about 0.5:1 to about 1.5:1 under isobutane-1-butene alkylation conversion conditions including temperature $T_2$, wherein $T_2<T_1$, to produce a second alkylate product enriched in isoparaffins having more than 5 carbon atoms;
   (g) contacting said third intermediate stream with excess isobutane in a third reaction zone containing $BF_3$ and $H_3PO_4$ in $BF_3$:$H_3PO_4$ molar ratios of from about 0.5:1 to about 1.5:1 under isobutene-2- butenes alkylation conversion conditions including temperature $T_3$, wherein $T_3 < T_2 < T_1$, to produce a third alkylate product enriched in isoparaffins having more than 5 carbon atoms; and (h) recovering said alkylate products from steps (e), (f), and (g).

2. The process of claim 1 wherein $T_1$ is from about 80° to about 120° F.

3. The process of claim 2 wherein $T_2$ is from about 80° to about 110° F.

4. The process of claim 3 wherein $T_3$ is from about 20 to about 60° F.

5. The process of claim 1 further comprising charging said isobutane to said first reaction zone at a rate sufficient to maintain an isobutane:propene molar ratio in said first reaction zone of from about 5:1 to about 20:1.

6. The process of claim 1 further comprising charging said isobutane to said second reaction zone at a rate sufficient to maintain an isobutane:1-butene molar ratio in said second reaction zone of from about 5:1 to about 20:1.

7. The process of claim 1 further comprising charging said isobutane to said third reaction zone at a rate sufficient to maintain an isobutane:2-butene molar ratio in said third reaction zone of from about 5:1 to about 20:1.

8. An isoparaffin-olefin alkylation process comprising the steps of:

(a) providing a feed comprising propene, 1-butene, 2-butenes, and isobutene;

(b) separating a first intermediate stream from said feed, said first intermediate stream being enriched in propene in comparison to said feed, to evolve a second propene-lean intermediate stream, said second propene-lean intermediate stream being lean in propene in comparison to said feed;

(c) contacting said second propene-lean intermediate stream with methanol in a first reaction zone containing an etherification catalyst under conversion conditions to selectively convert isobutene to methyl tertiary butyl ether;

(d) recovering methyl tertiary butyl ether from said second propene-lean intermediate stream;

(e) separating a third intermediate stream from said feed, said third intermediate stream being enriched in 1-butene in comparison to said feed;

(f) separating a fourth intermediate stream, said fourth intermediate stream being enriched in 2-butenes in comparison to said feed;

(g) contacting said first intermediate stream with excess isobutane in a first reaction zone containing $BF_3$ and $H_3PO_4$ in $BF_3:H_3PO_4$ molar ratios of from about 0.5:1 to about 1.5:1 under isobutane-propene alkylation conversion conditions including temperature $T_1$ to produce a first alkylate product enriched in isoparaffins having more than 4 carbon atoms;

(h) contacting said third intermediate stream with excess isobutane in a second reaction zone containing $BF_3$ and $H_3PO_4$ in $BF_3:H_3PO_4$ molar ratios of from about 0.5:1 to about 1.5:1 under isobutane-1-butene alkylation conversion conditions including temperature $T_2$, wherein $T_2 < T_1$, to produce a second alkylate product enriched in isoparaffins having more than 5 carbon atoms;

(i) contacting said fourth intermediate stream with excess isobutane in a third reaction zone containing $BF_3$ and $H_3PO_4$ in $BF_3:H_3PO_4$ molar ratios of from about 0.5:1 to about 1.5:1 under isobutane-2-butenes alkylation conversion conditions including temperature $T_3$, wherein $T_3 < T_2 < T_1$, to produce a third alkylate product enriched in isoparaffins having more than 5 carbon atoms; and (j) recovering said alkylate products from steps (g), (h), and (i).

9. The process of claim 8 wherein $T_1$ is from about 80° to about 120° F.

10. The process of claim 9 wherein $T_2$ is from about 80° to about 110° F.

11. The process of claim 10 wherein $T_3$ is from about 20° to about 60° F.

12. The process of claim 8 further comprising charging said isobutane to said first reaction zone at a rate sufficient to maintain an isobutane:propene molar ratio in said first reaction zone of from about 5:1 to about 20:1.

13. The process of claim 8 further comprising charging said isobutane to said second reaction zone at a rate sufficient to maintain an isobutane:1-butene molar ratio in said second reaction zone of from about 5:1 to about 20:1.

14. The process of claim 8 further comprising charging said isobutane to said third reaction zone at a rate sufficient to maintain an isobutane:2-butenes molar ratio in said third reaction zone of from about 5:1 to about 20:1.

15. A process for alkylating an isoparaffin with an olefin comprising the steps of:

(a) providing a feed comprising propene, 1-butene, and 2-butenes;

(b) separating a first intermediate stream from said feed, said first intermediate stream being enriched in propene and 1-butene in comparison to said feed;

(c) separating a second intermediate stream from said feed, said second intermediate stream being enriched in 2-butenes in comparison to said feed;

(d) contacting said first intermediate stream with excess isobutane in a first reaction zone containing $BF_3$ and $H_3PO_4$ in $BF_3:H_3PO_4$ molar ratios of from about 0.5:1 to about 1.5:1 under a first set of alkylation conversion conditions including temperature $T_1$ to produce a first alkylate product enriched in isoparaffins having more than 4 carbon atoms;

(e) contacting said second intermediate stream with excess isobutane in a second reaction zone containing $BF_3$ and $H_3PO_4$ in $BF_3:H_3PO_4$ molar ratios of from about 0.5:1 to about 1.5:1 under a second set of alkylation conversion conditions including temperature $T_2$, wherein $T_2 < T_1$, to produce a second alkylate product enriched in isoparaffins having more than 5 carbon atoms; and (g) recovering said alkylate products from steps (d) and (e).

16. The process of claim 15 wherein $T_1$ is from about 80° to about 110° F.

17. The process of claim 16 wherein $T_2$ is from about 20° to about 60° F.

18. The process of claim 15 further comprising charging said isobutane to said first reaction zone at a rate sufficient to maintain an isobutane:propene molar ratio in said first reaction zone of from about 5:1 to about 20:1.

19. The process of claim 15 further comprising charging said isobutane to said second reaction zone at a rate sufficient to maintain an isobutane:1-butene molar ratio in said second reaction zone of from about 5:1 to about 20:1.

* * * * *